United States Patent
Avegliano et al.

(10) Patent No.: US 10,600,509 B2
(45) Date of Patent: Mar. 24, 2020

(54) WEARABLE DEVICE FOR AUTOMATED CONSTRUCTION OF TRAINING PLANS AND METHOD OF USING THE SAME

(71) Applicant: INTERNATIONAL BUSINESS MACHINES CORPORATION, Armonk, NY (US)

(72) Inventors: Priscilla Barreira Avegliano, São Paulo (BR); Carlos Henrique Cardonha, São Paulo (BR); Matheus Palhares Viana, São Paulo (BR); Lucas Correia Villa Real, São Paulo (BR)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 284 days.

(21) Appl. No.: 15/439,546

(22) Filed: Feb. 22, 2017

(65) Prior Publication Data

US 2018/0236306 A1    Aug. 23, 2018

(51) Int. Cl.
*A63F 9/24* (2006.01)
*G16H 20/30* (2018.01)
*G09B 19/00* (2006.01)

(52) U.S. Cl.
CPC ......... *G16H 20/30* (2018.01); *G09B 19/0038* (2013.01)

(58) Field of Classification Search
CPC ............ A63B 24/0062; A63B 24/0075; A63B 2024/0065; A63B 24/0084; A63B 71/0622; A63B 2024/0093; G09B 5/02
See application file for complete search history.

(56) References Cited

U.S. PATENT DOCUMENTS

| 5,598,849 A | 2/1997 | Browne |
| 6,687,535 B2 | 2/2004 | Hautala et al. |
| 7,376,700 B1 | 5/2008 | Clark et al. |

(Continued)

FOREIGN PATENT DOCUMENTS

| CN | 104507052 | 4/2015 |
| EP | 1 159 989 | 12/2001 |

(Continued)

*Primary Examiner* — Steve Rowland
(74) *Attorney, Agent, or Firm* — F. Chau & Associates, LLC (57) ABSTRACT

A system for automatically generating an athletic training schedule includes a wearable device having one or more sensors for determining a quantity of athletic training performed by a user wearing the wearable device and an athletic performance of the user. A processor is configured to receive the quantity of athletic training performed and the athletic performance data from the wearable device, and to estimate a relationship between the quantity of athletic training performed and the athletic performance. A selection of a competitive target is received. A performance level of the selected competitive target is estimated. A minimum level of training needed to meet or exceed the estimated performance level is determined based on the estimated relationship between the quantity of athletic training performed and the athletic performance. The athletic training schedule is automatically generated based on the determined minimum level of training.

19 Claims, 4 Drawing Sheets

(56) References Cited

U.S. PATENT DOCUMENTS

| | | | |
|---|---|---|---|
| 7,942,784 B1* | 5/2011 | Hyde | G06F 19/3481 |
| | | | 482/9 |
| 10,363,453 B2 | 7/2019 | Fitzgerald et al. | |
| 10,391,361 B2 | 8/2019 | Watterson | |
| 2006/0205569 A1 | 9/2006 | Watterson et al. | |
| 2008/0071794 A1 | 3/2008 | Barnard | |
| 2008/0319661 A1 | 12/2008 | Werner et al. | |
| 2010/0273610 A1 | 10/2010 | Johnson | |
| 2011/0098156 A1 | 4/2011 | Ng et al. | |
| 2011/0172060 A1 | 7/2011 | Morales et al. | |
| 2011/0197157 A1* | 8/2011 | Hoffman | A63B 24/0062 |
| | | | 715/772 |
| 2011/0281249 A1* | 11/2011 | Gammell | G16H 10/20 |
| | | | 434/247 |
| 2011/0304497 A1* | 12/2011 | Molyneux | A43B 1/0054 |
| | | | 342/42 |
| 2012/0183939 A1* | 7/2012 | Aragones | A63B 24/0006 |
| | | | 434/247 |
| 2012/0251990 A1* | 10/2012 | Urbanowski | G06F 19/3481 |
| | | | 434/247 |
| 2012/0258433 A1* | 10/2012 | Hope | G06F 19/3481 |
| | | | 434/247 |
| 2012/0277891 A1* | 11/2012 | Aragones | G06F 19/3481 |
| | | | 700/91 |
| 2013/0040272 A1* | 2/2013 | Booher | G06F 19/3481 |
| | | | 434/254 |
| 2013/0138734 A1 | 5/2013 | Crivello et al. | |
| 2014/0107817 A1* | 4/2014 | Ellis | A61B 5/1038 |
| | | | 700/91 |
| 2016/0250519 A1 | 9/2016 | Watterson | |
| 2016/0287937 A1 | 10/2016 | Fitzgerald et al. | |

FOREIGN PATENT DOCUMENTS

| | | |
|---|---|---|
| EP | 1 897 598 | 3/2008 |
| WO | WO 02/062211 | 8/2002 |
| WO | WO 2007/099206 | 9/2007 |

* cited by examiner

WEARABLE DEVICE FOR AUTOMATED CONSTRUCTION OF TRAINING PLANS AND METHOD OF USING THE SAME

BACKGROUND

Technical Field

The present invention relates to wearable devices and, more specifically, to wearable devices for automated construction of training plans and method of using the wearable devices for the automated construction of the training plans.

Discussion of the Related Art

Wearable devices are small, computerized devices that are worn by the user to provide various input/output functions and computational tasks, often working in conjunction with another computerized device such as a smartphone.

Wearable devices have thus far been particularly popular for athletics and fitness activities, often having the ability to track steps, monitor heart rate and perform other key features that are helpful to athletes and exercisers. Popular examples of wearable devices used for this purpose include smartwatches such as the APPLE WATCH sold by Apple Inc. and fitness tracking wrist bands such as the FITBIT CHARGE sold by Fitbit.

While these devices may be worn by exercisers athletes at all levels, elite professional athletes often have access to coaches who may design for their athletes custom training plans to reach desired goals.

SUMMARY

A system for automatically generating an athletic training schedule includes a wearable device having one or more sensors for determining a quantity of athletic training performed by a user wearing the wearable device and an athletic performance of the user. A processor is configured to receive the quantity of athletic training performed and the athletic performance data from the wearable device, and to estimate a relationship between the quantity of athletic training performed and the athletic performance. A selection of a competitive target is received. A performance level of the selected competitive target is estimated. A minimum level of training needed to meet or exceed the estimated performance level is determined based on the estimated relationship between the quantity of athletic training performed and the athletic performance. The athletic training schedule is automatically generated based on the determined minimum level of training.

A computer program product for automatically generating an athletic training schedule includes a computer readable storage medium having program instructions embodied therewith. The program instructions are executable by a computer to cause the computer to receive, by the computer, data relating to a quantity of athletic training performed by a user and an athletic performance of the user. A relationship between the quantity of athletic training performed and the athletic performance is estimated by the computer. A selection of a competitive target is received by the computer. A performance level of the selected competitive target is estimated by the computer. A minimum level of training needed to meet or exceed the estimated performance level is determined by the computer, based on the estimated relationship between the quantity of athletic training performed and the athletic performance. The athletic training schedule is automatically generated, by the computer, based on the determined minimum level of training.

A method for automatically generating an athletic training includes receiving data relating to a quantity of training of a first type of activity performed by a user and an athletic performance of the user for the first type of activity. Data relating to a quantity of training of a second type of activity performed by the user and an athletic performance of the user for the second type of activity is received. A first relationship between the quantity of training of the first type of activity and the athletic performance of the first type of activity is estimated. A second relationship between the quantity of training of the second type of activity and the athletic performance of the second type of activity is estimated. A selection of a competitive target is received and a performance level of the selected competitive target is estimated. A minimum level of training needed to meet or exceed the estimated performance level is determined based on the first and second estimated relationships. The athletic training schedule is automatically generated based on the determined minimum level of training. The determining of the minimum level of training includes optimizing between training at the first activity and training at the second activity.

BRIEF DESCRIPTION OF THE SEVERAL VIEWS OF THE DRAWINGS

A more complete appreciation of the present invention and many of the attendant aspects thereof will be readily obtained as the same becomes better understood by reference to the following detailed description when considered in connection with the accompanying drawings, wherein.

DETAILED DESCRIPTION

In describing exemplary embodiments of the present invention illustrated in the drawings, specific terminology is employed for sake of clarity. However, the present invention is not intended to be limited to the illustrations or any specific terminology, and it is to be understood that each element includes all equivalents.

Exemplary embodiments of the present invention provide wearable devices and methods of using the same that may provide a user with automated construction of customized training plans specially tailored to getting the user to a desired state of preparedness prior to a certain time, for example, prior to an athletic event or competition, with the minimum possible effort.

Figure 1:
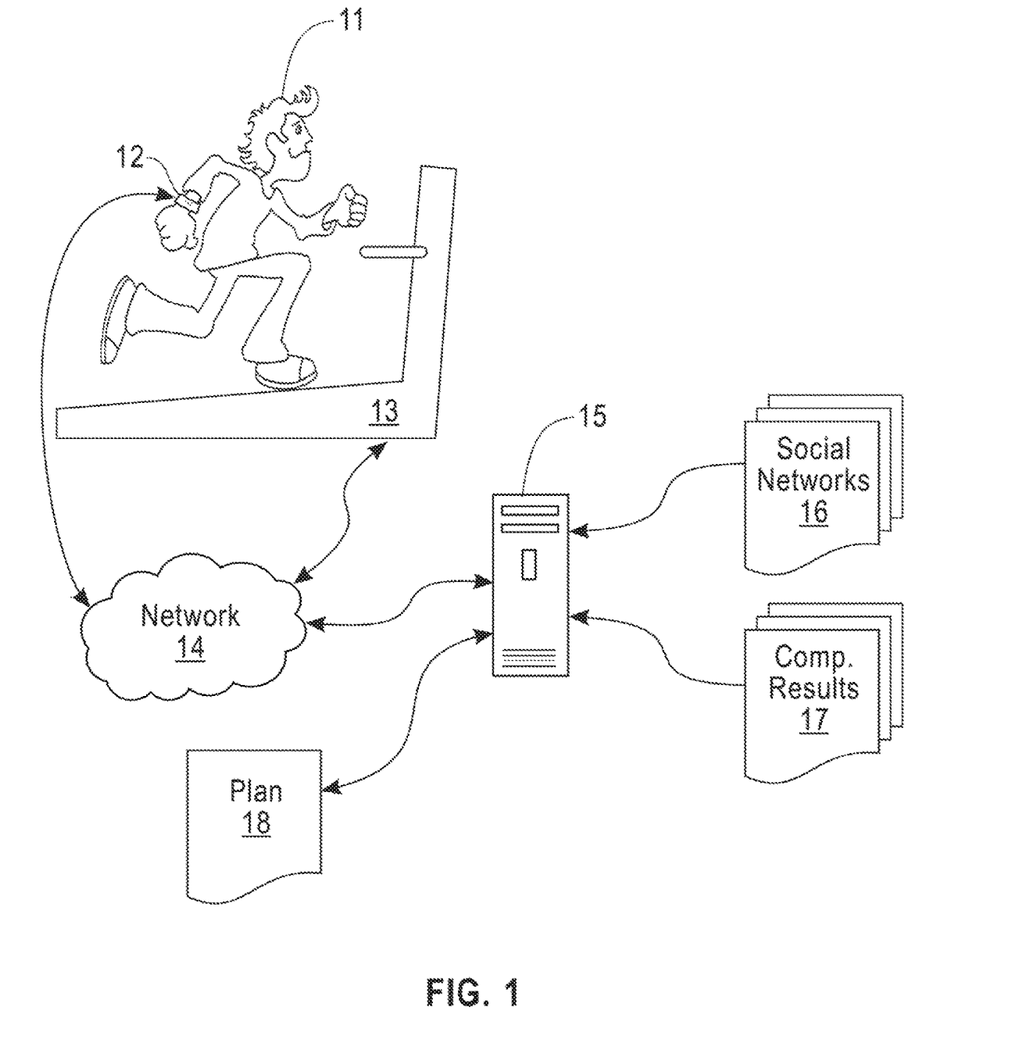
FIG. 1 is a schematic diagram illustrating a system, involving a wearable device, for automatically generating a training plan specifically tailored for a user to achieve a desired state of preparedness within a particular time horizon.

FIG. 1 is a schematic diagram illustrating a system, involving a wearable device, for automatically generating a training plan specifically tailored for a user to achieve a desired state of preparedness within a particular time horizon. While exemplary embodiments of the present invention may be described in terms of a runner training at running to achieve a desired speed, it is to be understood that running is used as an example of any arbitrary sport or physical activity, and the systems and methods described herein may be applied to any arbitrary sport or activity.

A user 11, who may be an athlete, may wear a wearable device 12 such as a smartwatch or fitness tracing band. The wearable device 12 may acquire sensory information such as accelerometer data, heartrate data, GPS coordinate data, and the like. The wearable device 12 may send this data to a central serve 15. The wearable device may be in communication with the central server over a computer network 14. The computer network 14 may be a local area network (LAN) such as a WiFi network, and/or the computer network 14 may be a wide area network (WAN) such as the Internet.

The wearable device 12 may communicate directly with the computer network 14 using wireless radios disposed therein or the wearable device 12 may communicate with the computer network 14 via a smartphone device.

The user 11 may also use a connected exercise machine 13 such as a treadmill. The connected exercise machine 13 may be able to report to the central server 15 on the manner in which it is being used and may be programmed to operate in a particular manner by the instructions of the central server 15. The connected exercise machine 13 may communicate with the central server 15, for example, over the computer network 14.

The central server 15 may be embodied as a cloud-based service or may be a computer that is local to the location of the user 11. The central server 15 may also be embodied within the wearable device 12, where processing power allows for this possibility.

The central server 15 receives input from the wearable device 12 and/or the connected exercise machine 13, and obtains data from various external sources such as social networks 16 and athletic competition results 17, and uses this information to automatically generate a training plan 18 according to various approaches that are described in detail below. The training plan 18 may then be communicated to the user 11, for example, via the wearable device 12 and/or may be used to automatically control the mode of operation of the connected exercise machine 13. The social networks 16 and the competition results 17 may be accessed by the central server 15 via the computer network 14 or this information may be accumulated and/or curated by another source, such as another cloud-based service. The user may also interface with the central server 15 via the wearable device 12 or through another computerized device such as a smartphone or personal computer.

Figure 2:
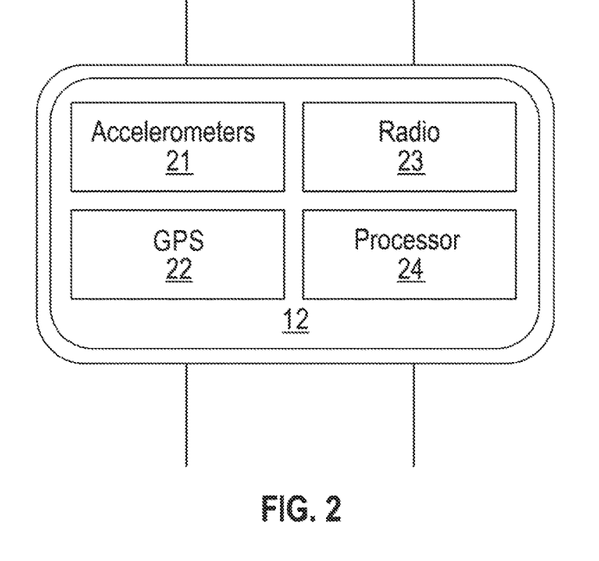
FIG. 2 illustrates a detailed view of the wearable device shown in FIG. 1.

FIG. 2 is a more detailed view of the wearable device 12 shown in FIG. 1. As illustrated, the wearable device 12 may include accelerometers 21. Accelerometers may be used to track movement so that steps taken may be determined. In addition to the accelerometers 21, various other sensors may be included such as heart rate monitors, and a global positioning service (GPS) receiver 22 for determining location. The wearable device 12 may additionally include various radios 23 such as a Bluetooth radio for communicating with a smartphone, a WiFi radio for communicating with a LAN, and/or a cellular radio for communicating with a cellular base station, for example, to connect to the Internet.

Figure 3:
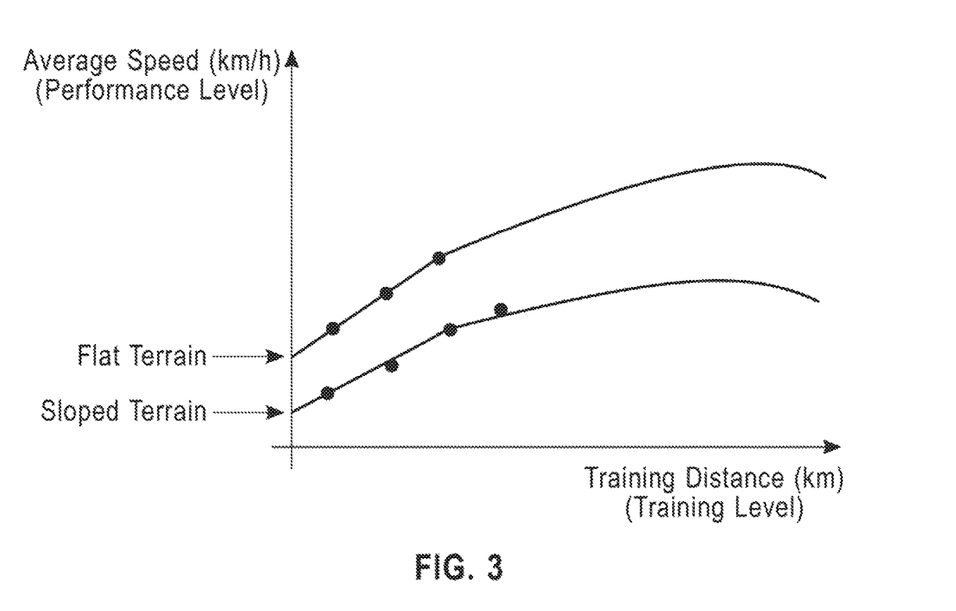
FIG. 3 is a graph illustrating two training-performance curves in accordance with exemplary embodiments of the present invention.

As described above, exemplary embodiments of the present invention may use the system described above to automatically generate a training plan that is specifically tailored for the user to achieve a desired performance goal within a particular period of time. This is performed, at least in part, by calculating, for the user, one or more training-performance curves. Each training-performance curve shows, for the particular user, and the particular activity or sub-activity, an estimation of how much training is required to achieve a particular performance goal. FIG. 3 is a graph illustrating two training-performance curves in accordance with exemplary embodiments of the present invention.

The training-performance curves of FIG. 3 pertain to the activity of running, although it could easily be modified for any other sport or activity. The extent of training is expressed in terms of training distance, here provided along the x-axis. The extent of training, here, is expressed in kilometers (km), however, other metrics could be used such as hours ran, etc.

The performance level is here expressed in terms of speed, measured in kilometers-per-hour (km/h) and is shown along the y-axis. However, performance level may be expressed by other metrics such as total time to complete a course.

The training-performance curve therefore shows us how much training is required to achieve a desired performance level. Ways in which the desired performance level is selected are described in greater detail below, however, for the desired performance level, the training-performance curve tells us approximately how much training is needed.

The training-performance curve may be generated based on one or more data points, which are shown below as the star-shaped markers. The data points may be acquired by the wearable device while the user is engaged in the aforementioned activity, here running. As the wearable device reports on distance ran and running speed (e.g. based on time of start and end), the central server can accumulate the data points and extrapolate the training-performance curve therefrom.

The training-performance curve may be fitted to the available data points using various curve-fitting techniques, with the understanding that the general shape of the curve is likely to be a concave curve that at first has a positive slope, and later, has a negative slope. As it might be the case that the available data points are insufficient to span across all training levels, a shape of the curve may be extrapolated based on the shape of the training-performance curve of other athletes. To this end, other athletes may be clustered by such factors as age, size, running experience, etc. and then an average training-performance curve for the cluster most similar to the instant user may be fitted to the instant user's available data points. In this way, the user's training-performance curve may be estimated, even where insufficient data points exist to fit the full training-performance curve.

The data points for the other athletes may be obtained, for example, as other athletes use the system described herein. Also, relevant data points may be gathered from social media and other published sources.

A given user may have multiple training-performance curves, even for a single activity. For example, where the user is running, a first training-performance curve may be determined for running on flat terrain, and a second training-performance curve may be determined for sloped terrain, for example, as shown in FIG. 3. Each training-performance curve may be fitted to data points representative of running on the particular terrain type. According to some exemplary embodiments of the present invention, the particular terrain type may be known from the sensor data of the wearable device, which may use GPS data overlaid with known elevation data, which may be gleamed from altitude information obtained from the GPS data and/or air pressure data, or by user input, for example, via the wearable device. Where the connected exercise machine is used, the connected exercise machine may automatically report on incline or may be automatically set to a desired level of incline to obtain the data points needed to generate the training-performance curve.

According to one exemplary embodiment of the present invention, the central server may run a program on the connected exercise machine, that is designed to obtain enough data points needed to approximate the desired training-performance curves for the user, for example, both the sloped terrain training-performance curve and the flat terrain training-performance curve. This may be seen as a calibration stage involving data points created by the programming and carried out on the connected exercise machine. From this, the training plan may be automatically generated, with the training plan not necessarily having to be followed on the connected exercise machine, this is to say, the user may carry out the automatically generated training plan by running on the road or track, rather than on the connected exercise machine.

Figure 4:
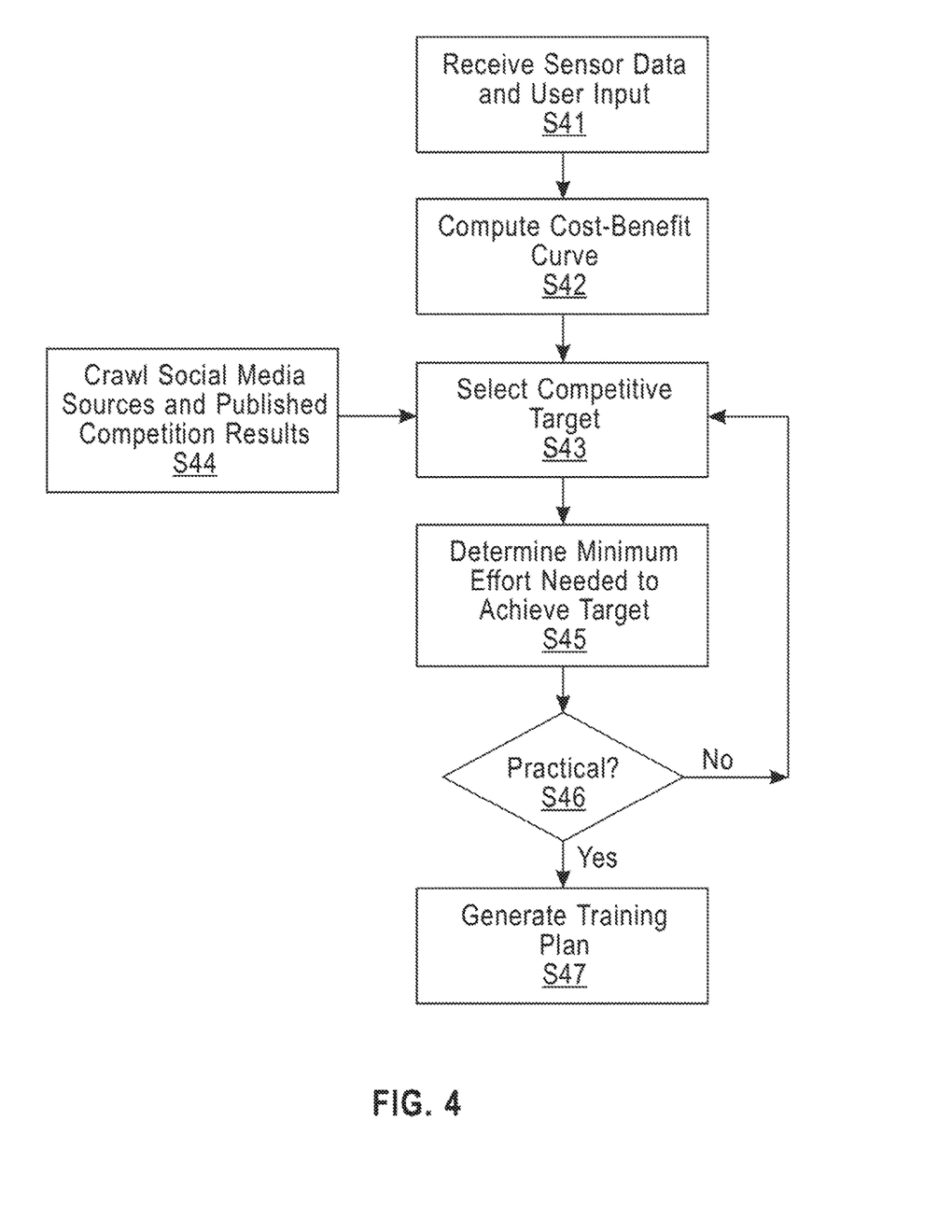
FIG. 4 is a flow chart illustrating a method for automatically generating training plans in accordance with exemplary embodiments of the present invention.

FIG. 4 is a flow chart illustrating a method for automatically generating training plans in accordance with exemplary embodiments of the present invention. First, sensor data may be received from a wearable device worn by a user, usage information may be received from a connected exercise machine, and/or user input may be provided (S41). This information may include one or more data points representing a level of training (e.g. distance) and a level of performance (e.g. speed) associated with the level of training. The one or more data points may include one or more different sports or other athletic endeavors or one or more different manners of performing the same activity (e.g. running on an incline and running on a flat surface).

From the data points, one or more cost-benefit curves may be computed for the particular user (S42). The cost-benefit curves may be computed by curve-fitting to the available data points and/or using cost-benefit curves from clustered individuals to augment the curve fitting.

The user may then select a competitive target (S43). This may include entering in either a desired level of performance such as a finishing time or, according to some exemplary embodiments of the present invention, entering in a desired finishing place and/or a particular opponent the user is looking to match or beat. The user may select from a list of known opponents for the particular competition, which may be obtained by the system from social media sources and/or a published register of event participants. This information may also be estimated from past events. According to exemplary embodiments of the present invention, various social media sources may be crawled to find this information and/or competition registrations or results from past competitions may be examined (S44).

After the competitive target has been so-selected, a minimum training effort needed to achieve the selected target is determined. This minimum training effort may be calculated by looking at the selected opponent and estimating his or her performance on the coming event by analyzing the crawled social media sources and published competition results and using this information to determine a desired level of performance (e.g. a desired speed or finishing time). Where the user has selected the desired level of performance rather than selecting an opponent, this information may already be known. Where the user has selected a finishing rank (e.g. first, second, third place, etc.), then the data from crawling social media sources, published competition results/registrations may be used to estimate performance of all top competitors of the event so that the desired level of performance may be known.

Once the desired level of performance is understood, for example, in terms of finishing time or speed, whether it is explicitly provided by the user or determined as described above, the user's cost-benefit curves may be referenced to determine a minimum amount of training needed to obtain the desired level of performance (S45). Multiple cost-benefit curves may be used as the event may combine different activities (e.g. a triathlon) or the event may combine different sub-activities (e.g. running on a flat surface and running on an inclined surface). The composition of the event may be determined, for example, from the crawled data, and then the relevant components of each different activity or sub-activity may be understood and applied to the user's objectives.

A determination may then be made as to whether the desired level of performance is practical (S46). The desired level of performance might not be practical if it exceeds a top potential of the user or if it requires a level of training that exceeds an amount of time that is available to the user for the purpose of training. If the desired level of performance is determined not to be practical (No, S46), then the user may be prompted to enter a different competitive target (S43). If the desired level of performance is determined to be practical (Yes, S46), then the training plan may be automatically generated (S47).

According to an alternative approach, however, the determination as to which desired levels of performance are practical may be made prior to having the user select the competitive target, and the user's input may be limited to the set of competitive targets that are practical. To this end, the user may also be prompted to provide a maximum available level of training so that the display of options are more appropriate for the particular user. For example, those opponents that represent a performance level unachievable by the user may be displayed as non-selectable and then, after the user provides a maximum available level of training, those opponents that represent a performance level that cannot be achieved within the available level of training may also be rendered non-selectable.

As discussed above, the training plan may be generated by determining what training level will likely provide the desired performance level, and then a generic training schedule may be modified (e.g. expanded or compressed) according to the determined training level. The final training plan may then be displayed, for example, on the wearable device of the use or used to automatically set the training program of the connected exercise machine.

The training plan may also be optimized so that the limited available level of training is best split between each of the various different activities or sub-activities. By understanding how much performance gain is to be achieved by training each activity/sub-activity, the training schedule may be focused on the activity/sub-activity that will provide the greatest overall advantage. For example, the ratio of flat track to inclined track in the event may be known, and the total time for the user to complete the track may be known with reference to the cost-benefit curves for each of the flat running and inclined running. It can then be determined where each successive increment of training is best applied e.g. by determining whether the successive increment of training would better increase total track performance if applied to flat training or to inclined training. In this way, the present system can provide the optimal training plan, in terms of flat training and inclined training, to exceed the expected performance of the selected competitor, with minimal training effort.

Figure 5:
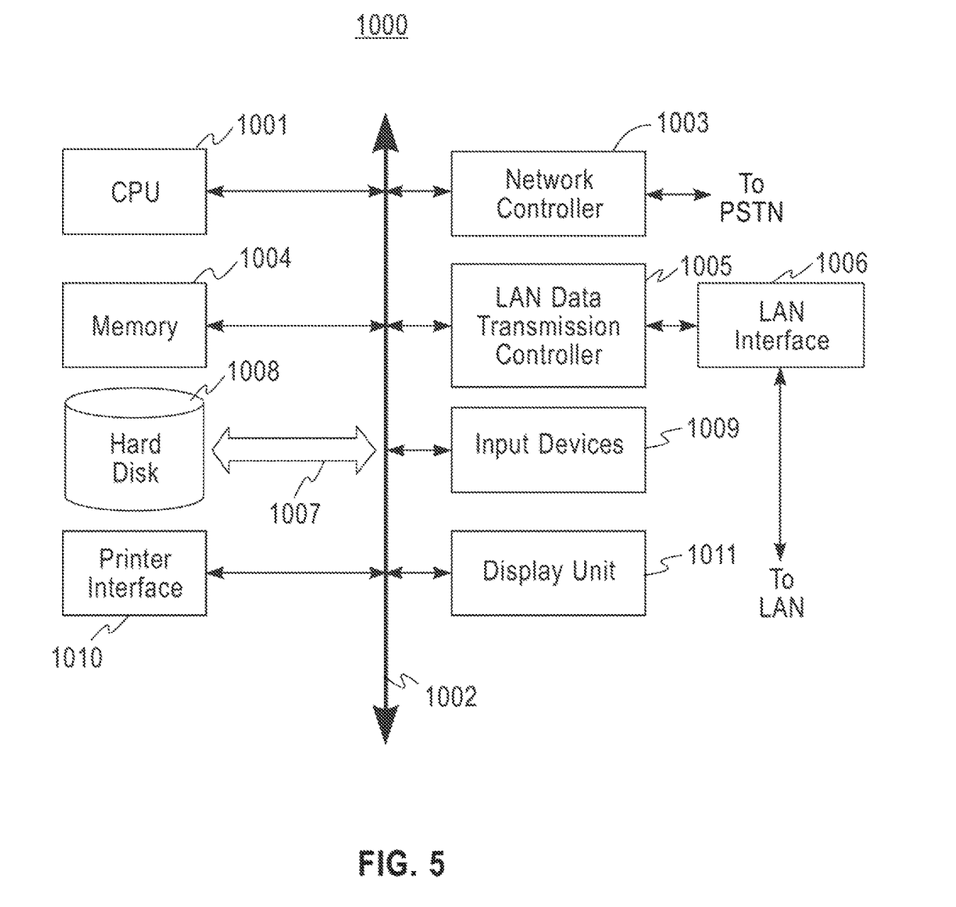
FIG. 5 shows an example of a computer system capable of implementing the method and apparatus according to embodiments of the present disclosure.

FIG. 5 shows another example of a system in accordance with some embodiments of the present invention. By way of overview, some embodiments of the present invention may be implemented in the form of a software application running on one or more (e.g., a "cloud" of) computer system(s), for example, mainframe(s), personal computer(s) (PC), handheld computer(s), client(s), server(s), peer-devices, etc. The software application may be implemented as computer readable/executable instructions stored on a computer readable storage media (discussed in more detail below) that is locally accessible by the computer system and/or remotely accessible via a hard wired or wireless connection to a network, for example, a local area network, or the Internet.

Referring now to FIG. 5, a computer system (referred to generally as system 1000) may include, for example, a processor e.g., central processing unit (CPU) 1001, memory 1004 such as a random access memory (RAM), a printer interface 1010, a display unit 1011, a local area network (LAN) data transmission controller 1005, which is operably coupled to a LAN interface 1006 which can be further coupled to a LAN, a network controller 1003 that may provide for communication with a Public Switched Telephone Network (PSTN), one or more input devices 1009, for example, a keyboard, mouse etc., and a bus 1002 for operably connecting various subsystems/components. As shown, the system 1000 may also be connected via a link 1007 to a non-volatile data store, for example, hard disk, 1008.

In some embodiments, a software application is stored in memory 1004 that when executed by CPU 1001, causes the system to perform a computer-implemented method described with reference to FIG. 4.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Exemplary embodiments described herein are illustrative, and many variations can be introduced without departing from the spirit of the invention or from the scope of the appended claims. For example, elements and/or features of different exemplary embodiments may be combined with each other and/or substituted for each other within the scope of this invention and appended claims.

What is claimed is:

1. A system for automatically generating an athletic training schedule, comprising:
   a wearable device, including one or more sensors for determining a quantity of athletic training performed by a user wearing the wearable device and an athletic performance of the user; and
   a processor configured to:
   receive the quantity of athletic training performed and the athletic performance data from the wearable device, and to estimate a relationship between the quantity of athletic training performed and an increase in the athletic performance by fitting a known curve relating athletic training performed and an increase in athletic performance to the received quantity of athletic training performed and the athletic performance data from the wearable device, wherein the athletic performance data is an indication of athletic speed or a time required to complete an athletic event;
   receive a selection of a competitive target;
   estimating a performance level of the selected competitive target;
   determine a minimum level of training needed to meet or exceed the estimated performance level, based on the estimated relationship between the quantity of athletic training performed and the athletic performance; and
   automatically generate the athletic training schedule based on the determined minimum level of training.

2. The system of claim 1, wherein the one or more sensors for determining a quantity of athletic training performed by a user wearing the wearable device and an athletic performance of the user include an accelerometer or a GPS receiver.

3. The system of claim 1, additionally comprising a computer network-connected exercise machine configured to further determine the quantity of athletic training performed by the user and the athletic performance of the user, wherein the processor is further configured to estimate the relationship between the quantity of athletic training performed and the athletic performance based on data received from the wearable device and data received from the computer network-connected exercise machine.

4. The system of claim 3, wherein the computer network-connected exercise machine is configured to receive the automatically generated athletic training schedule and operate an exercise program therefrom.

5. The system of claim 1, wherein the wearable device is configured to receive the automatically generated athletic training schedule and guide the user in performing the automatically generated athletic training schedule.

6. The system of claim 1, wherein the processor is disposed within the wearable device.

7. The system of claim 1, wherein the processor is disposed within a server that is in communication with the wearable device over a computer network.

8. The system of claim 1, wherein the relationship between the quantity of athletic training performed and the athletic performance is estimated by fitting the quantity of athletic training performed and the athletic performance data received from the wearable device with curves determined from comparable data of athletes identified as being similar to the user.

9. The system of claim 1, wherein the selection of the competitive target is a selection of a desired result of a particular athletic competitive event.

10. The system of claim 9, wherein the desired result is a finishing place, score, or exceeding a performance of a particular individual.

11. The system of claim 10, wherein the performance of the particular individual is estimated based on past performance of the particular individual.

12. The system of claim 11, wherein the past performance of the particular individual is estimated from social media data or published competition results that have been automatically obtained.

13. A computer program product for automatically generating an athletic training schedule, the computer program product comprising a computer readable storage medium having program instructions embodied therewith, the program instructions executable by a computer to cause the computer to:
   receive, by the computer, data relating to a quantity of athletic training performed by a user and an athletic performance of the user;
   estimate, by the computer, a relationship between the quantity of athletic training performed and the athletic performance;
   receive, by the computer, a selection of a competitive target; estimate, by the computer, a performance level of the selected competitive target; determine, by the computer, a minimum level of training needed to meet or exceed the estimated performance level, based on the estimated relationship between the quantity of athletic training performed and the athletic performance; and automatically generate, by the computer, the athletic training schedule based on the determined minimum level of training, wherein the relationship between the quantity of athletic training performed and the athletic performance is estimated, by the computer, by fitting the quantity of athletic training performed and the athletic performance data received from the wearable device with curves determined from comparable data of athletes identified as being similar to the user.

14. The computer program product of claim 13, wherein the selection of the competitive target is a selection of a desired result of a particular athletic competitive event, the desired result is a finishing place, score, or exceeding a performance of a particular individual, and the performance of the particular individual is estimated based on past performance of the particular individual.

15. The computer program product of claim 14, wherein the past performance of the particular individual is estimated from social media data or published competition results that have been automatically obtained.

16. A method for automatically generating an athletic training schedule, comprising:

receiving data relating to a quantity of training of a first type of activity performed by a user and an athletic performance of the user for the first type of activity;

receiving data relating to a quantity of training of a second type of activity performed by the user and an athletic performance of the user for the second type of activity;

estimating a first relationship between the quantity of training of the first type of activity and the athletic performance of the first type of activity;

estimating a second relationship between the quantity of training of the second type of activity and the athletic performance of the second type of activity;

receiving a selection of a competitive target and estimating a performance level of the selected competitive target;

determining a minimum level of training needed to meet or exceed the estimated performance level, based on the first and second estimated relationships; and automatically generating the athletic training schedule based on the determined minimum level of training, wherein the determining of the minimum level of training includes optimizing between training at the first activity and training at the second activity, wherein the first relationship between the quantity of athletic training of the first type of activity performed and the athletic performance of the first type of activity performed is estimated by fitting the quantity of athletic training of the first type of activity performed and the athletic performance data of the first type of activity performed received from the wearable device with curves determined from comparable data of athletes identified as being similar to the user.

17. The method of claim 16, wherein the selection of the competitive target is a selection of a desired result of a particular athletic competitive event, the desired result is a finishing place, score, or exceeding a performance of a particular individual, and the performance of the particular individual is estimated based on past performance of the particular individual.

18. The method of claim 17, wherein in determining the minimum level of training needed to meet or exceed the estimated performance level, a ratio of the first activity to the second activity of the particular athletic competitive event is considered.

19. The method of claim 16, wherein the athletic training schedule includes a first level of training for the first activity and a second level of training for the second activity.

* * * * *